United States Patent [19]

Geist et al.

[11] Patent Number: 4,772,377
[45] Date of Patent: Sep. 20, 1988

[54] MEMBRANE ANCHOR FOR ION-SELECTIVE ELECTRODES

[75] Inventors: Jill M. Geist, Wildwood; Thomas G. Schapira, Lindenhurst, both of Ill.

[73] Assignee: Abbott Laboratories, Abbott Park, Ill.

[21] Appl. No.: 53,454

[22] Filed: May 22, 1987

[51] Int. Cl.⁴ ............................................. G01N 27/26
[52] U.S. Cl. ..................................... 204/415; 204/416; 204/418; 204/435
[58] Field of Search ................ 204/1 T, 415, 416, 418, 204/435

[56] References Cited

U.S. PATENT DOCUMENTS

| | | | |
|---|---|---|---|
| 4,180,771 | 12/1979 | Guckel | 324/715 N |
| 4,393,130 | 7/1983 | Ho et al. | 430/313 |
| 4,449,011 | 5/1984 | Kratochvil et al. | 174/52 PE |
| 4,454,007 | 6/1984 | Pace | 204/1 T |
| 4,456,522 | 6/1984 | Blackburn . | |
| 4,486,292 | 12/1984 | Blackburn | 204/416 |
| 4,683,048 | 7/1987 | Yamada et al. | 204/416 |

Primary Examiner—R. L. Andrews
Attorney, Agent, or Firm—Dennis K. Shelton; Martin L. Katz

[57] ABSTRACT

A membrane anchor for an ion-selective electrode may be formed by intersolubilizing an ion-selective membrane lying above a sensing pad with a region of thermoplastic material laterally disposed around the membrane. A first layer of electrically insulating thermoset material lies beneath the thermoplastic material and in intimate contact with an electrically insulating substrate. A second layer of exposed thermoset material lies above the thermoplastic material and contacts the first layer of thermoset material around the entire lateral perimeter of the thermoset material.

The membrane anchor may be usefully employed with an ion-selective electrode having an electrically insulating substrate with a substantially planar surface and having non-metallic means for sensing a potential affixed to the surface beneath an ion-sensitive membrane.

9 Claims, 2 Drawing Sheets

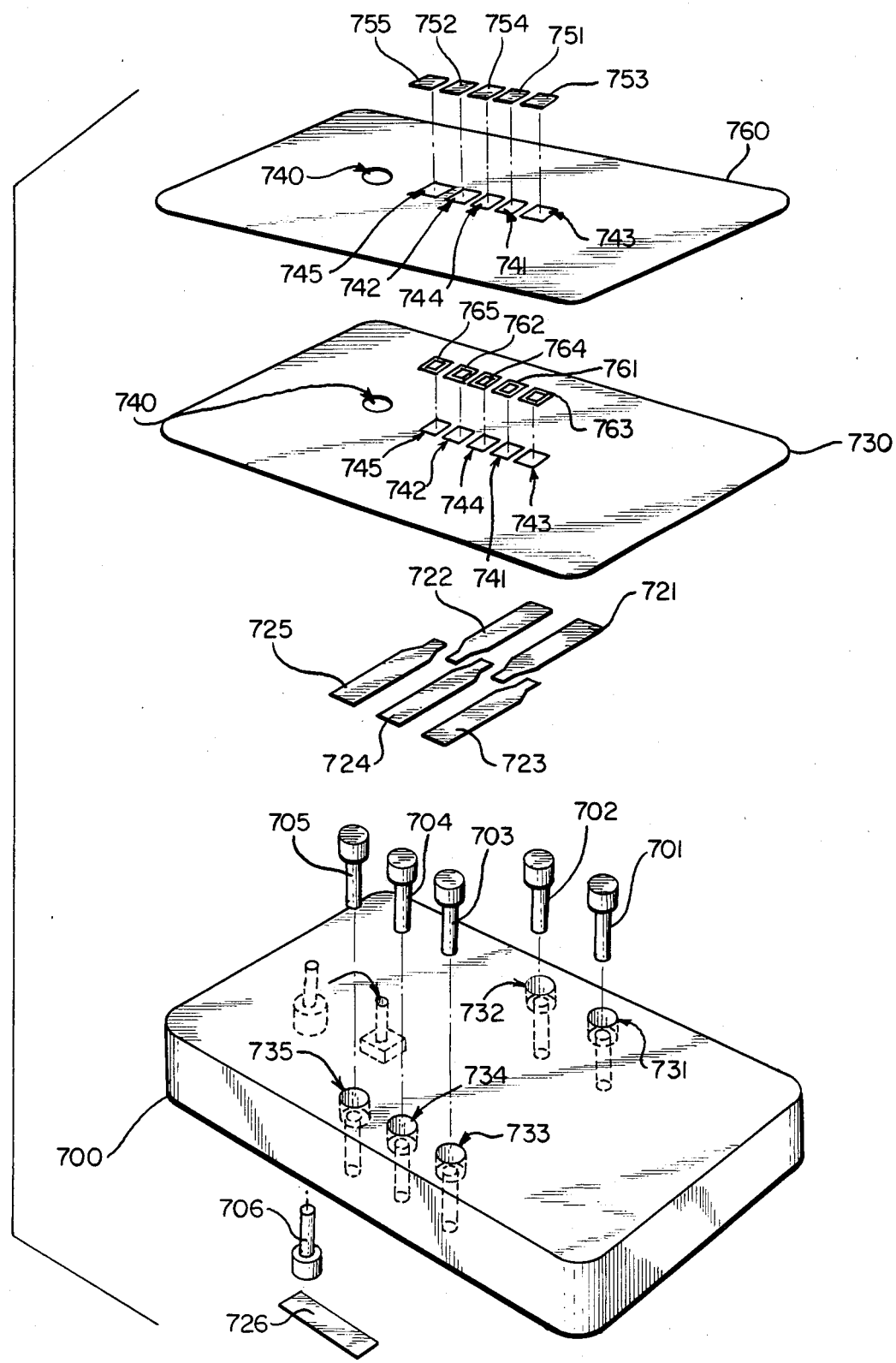

MEMBRANE ANCHOR FOR ION-SELECTIVE ELECTRODES

BACKGROUND OF THE INVENTION

The present invention pertains in general to ion-selective membranes and in particular to insulative layers associated with ion-selective membranes and conductive patterns suitable for fabrication of ion-selective electrodes.

When placed in contact with a solution, ion-selective electrodes provide an electrical output which is a function of the concentration of a particular ion in the solution. In such electrodes an output potential ("Y") is measured between a "sensing element," responsive to the concentration of the particular ion, and a "reference element," held at a constant potential, Y may be plotted against the base 10 logarithm of the concentration of the ion ("X") as a straight line having a slope ("M") and y-axis intercept ("B") as expressed in the Nernst equation:

$$Y = M (\log_{10} X) + B$$

Ion-selective electrodes conventionally have an internal reference element of Ag/AgCl immersed in a solution or gel of chloride ion. The chloride ion solution or gel holds the reference element at a constant potential, providing that the chloride concentration and thermodynamic functions, such as temperature and pressure, are held constant. An ion-selective glass or membrane sensing element is placed in contact with the solution or gel to form an interface between the test solution and this internal filling solution. However, this conventional design is complex to manufacture and difficult to miniaturize.

In the fabrication of ion-selective electrodes a major problem is leakage at the interface of the ion-selective membrane and the insulative surface. This leakage causes corrosion and drift of the ion-selective electrode. Various attempts to prevent leakage at the membrane interface are described in the literature. U.S. Pat. No. 4,180,771 describes placing the gate lead on the opposite face of FET device to isolate the ion-sensing area. U.S. Pat. No. 4,449,011 to Kratachvil describes placing an insulating tape around the ion-sensing areas in an attempt to prevent moisture leakage.

U.S. Pat. No. 4,393,130 to Ho et al, provides a dry film photoresist laminate which requires photo processing and etching to form a window around the ion-sensing areas for placement of the ion-selective membrane. A process for encapsulating ion-selective electrodes with thixotropic material having a window for an ion-selective membrane is also disclosed.

U.S. Pat. Nos. 4,456,522 and 4,486,292 to Blackburn describe a method for spinning a polyimide layer onto a conductor which is then chemically etched to leave a floating polyimide mesh. The mesh provides a physical support for a polymeric ion-selective membrane.

U.S. Pat. No. 4,454,007 to Pace describes a system whereby the ion-selective membrane is anchored to a conductor by intersolubilization. However, moisture may penetrate between the membrane and insulating layers to corrode the contacts.

In all these cases effective anchoring of the ion-selective membrane and insulation of the conductors are not achieved. Therefore, new systems for anchoring ion-selective membranes are desirable. The present invention describes a system comprising a plurality of insulative layers deposited over the substrate where at least a portion of one of the layers is intersolubilized with ion-selective membrane. This system is effective for preventing leakage between the membrane and the insulating layers.

SUMMARY OF THE INVENTION

The present invention provides an anchored ion-selective membrane having an electrically insulating substrate with a substantially planar surface. Means, affixed to said surface, for sensing a potential include the anchored ion-selective membrane and a conductor coupled to the means for sensing. An electrically insulating layer covers at least a portion of the conductor wherein the electrically insulating layer includes a first stratum affixed to the surface, a second stratum intersolubilized with the ion-selective membrane, and a third stratum covering the first stratum and the second stratum. The ion-selective electrode preferably has means for sensing which includes a conductive termination which is preferably non-metallic.

The ion-selective electrode having an anchored membrane according to the present invention may have means for sensing including a field effect transistor and a conductive termination, preferably non-metallic, coupled to an electrode of the field effect transistor.

The ion-sensitive electrode having an anchored membrane according to the present invention may have means for sensing which includes a non-metallic, offset gate connected to a bulk electrode of a ChemFET and an exposed ion-selective membrane layer covering the offset gate.

In a preferred embodiment of the present invention, metalization is not used on the surface of the device which contacts an analyte. Rather, a non-metallic, conductive material forms the conductive portions of the sensing element contacting the anchored membrane and also forms the leads between the anchored membrane and a conductor passing through the insulating substrate to a surface of the device, which surface is shielded from the analyte. The non-metallic conductive material may include graphite in a suitable supportive and binding matrix or may include a conductive polymer, such as polyacetylene, and polypyrrole among others.

BRIEF DESCRIPTION OF THE DRAWINGS

FIG. 3 is an exploded ion-selective electrode view of an ISE with no electronics on the substrate.

DETAILED DESCRIPTION

Figure 1:
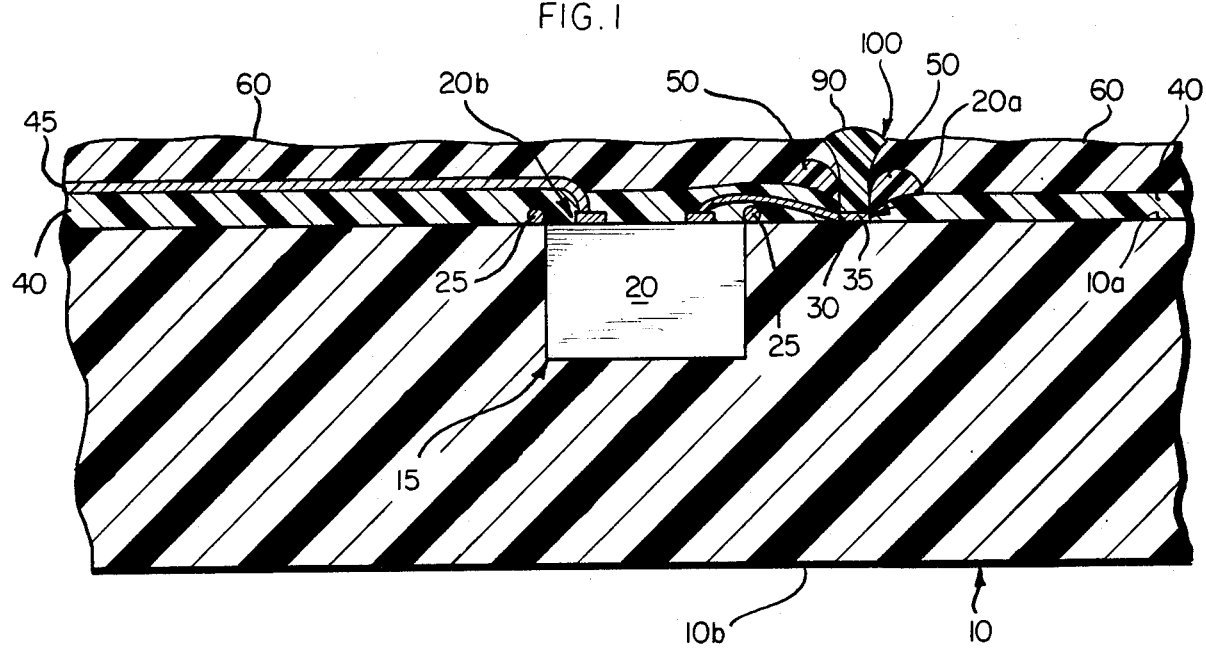
FIG. 1 is a cross-sectional view of a FET device according to the present invention.

The present invention provides a screen-printable chemical anchor and well for containing a polymeric membrane which is specially formulated for application on a semiconductor chip or on a thin- or thick-film substrate in order to detect specific chemistries such as ions, electrolytes, metabotites, enzymes, proteins, and blood gasses.

Screen printing is used in the fabrication of thick film microelectronics such as hybrids, and is an established technique for the laydown of thixotropic electronic materials. Construction of a membrane anchor/well by screen printing simplifies physical application of the membrane, controls the geometry of the membrane, controls the thickness of membrane, and provides physical support for the membrane. Screen printing of a membrane anchor and well permits unlimited variation in planar geometry of sensing areas without a threat to the membrane, and also permits a virtually unlimited number of sensors per device. Moreover, encapsulation and definition of sensor areas are accomplished simultaneously and cross contamination of various membranes on one device is prevented.

In addition, specific polymeric materials may be selected to provide for: chemical adherence between membrane and encapsulant or anchor; physical protection of sensing surface; and electrical integrity of substrate, chip circuitry and external electrical connections from adverse environments.

The present invention employs a solvent sensitive material (which may be a thermoplastic polymer) to encapsulate part of overcoat material in a zone around the sensing areas. When implemented by screen printing, a screening pass is made after or between undercoat and overcoat passes. A solvent in the membrane formulation partially dissolves the thermoplastic material and thus provides an "anchor" for improved adhesion of the membrane. This adhesion also improves moisture resistance and eliminates leakage current failure of the coating. There is a chemical adherence between the membrane and the material encapsulating conductive areas.

A deep membrane well prevents cross contamination of the membranes and provides physical support for the membranes.

In a preferred embodiment, an insulating substrate is cleaned ultrasonically and by vapor degreasing using an appropriate solvent (such as Freon TA). The substrate is annealed at 160° C. for 90 minutes and slow cooled to room temperature. The substrate is used as a base for a screen printing pattern. The screens used consist of standard mesh materials with emulsions as known in the art. Inks for various layers are formulated to meet requirements for thick film printing. Standard screen printing apparatus are adjusted to meet the print requirements of the various inks and patterns employed.

In a preferred embodiment, graphite particles are dispersed in a suitable matrix for printing straight line patterns on a substrate. Three insulating layers are then spread or printed over the graphite and substrate in a pattern which forms a window or opening over an area of the graphite. In this embodiment the intermediate layer is choosen such that it intersolubilizes with the ion-selective membrane to effectively anchor the membrane to the insulating layers. The insulating layers are printed to a total thickness, varying from 15 to 500 microns, to define a well over the opening. The substrate and/or insulating design also permits electrical contact of an analyte with the graphite pattern directly below the well or at some offset.

To remove potential contamination (particulate, organic, etc.), the opening above the conductor is rinsed with an appropriate solvent (such as acetone, MEK or THF). After rinsing, a membrane formulated as known in the art, is applied in liquid form over the conductor surface in the well area. Approximately 0.1 microliters of the membrane formula may be applied in the well. Depending on membrane formula, multiple applications of a membrane may be used in the same well to provide the proper integrity.

As examples, some useful membrane formulas are: for $Na^+$, 140 mg dibutyl sebacate, 60 mg PCV, 1 ml THF, and 2 mg of a $Na^+$ ionophore; for pH, 20 mg tridodecylamine, 132 mg dibutyl sebacate, 1 ml THF, 51 mg PVC and 1.4 mg tetraphenylborate; for $K^+$, 140 mg di-2-ethylhexyladipate, 1 ml THF, 60 mg PVC and 2.0 valinomycin; and for $Ca^{++}$, 41.8 mg nitrophenyloctylether, 6.6 mg PVC, 0.2 m/THF, 4.7 mg $Ca^{++}$ ionophore, and 0.47 mg sodium tetraphenylborate. After applying the membrane, the solvent is allowed to evaporate out of the membrane. After evaporating the solvent, membranes may be conditioned in appropriate solutions as known in the art.

FIG. 1 depicts an embodiment of a sensing element according to the present invention. In FIG. 1, a portion of an electrically insulating substrate 10 is shown to have a first planar surface 10a and a second planar surface 10b. As indicated in FIG. 1, surfaces 10a and 10b may respectively be an obverse and a reverse surface of a planar substrate 10. Into a depression 15 in surface 10a, a field effect transistor (FET) 20, surrounded by a screen printed insulating underring 25, is inserted substantially flush with surface 10a. A conductive finger 30 (preferably formed by a graphite ink) passes along surface 10a between a gate contact of FET 20 and an offset gate 35. Upon this construction, the rest of the sensing element is formed by layers or deposits of materials having the appropriate properties.

An electrically insulating undercoat 40 covers all portions of semiconductor 20 which are exposed at surface 10a except for an aperture 20a around an offset gate 35 and for an aperture 20b around a source contact of FET 20 and an region 20c (not shown) around a drain contact (not shown) of FET 20 and similarly for a region 20d (not shown) around a bulk contact (not shown) of FET 20. A lead 45 provides an external electrical connection for the source (not shown) of FET 20. A similar lead (not shown) provides an external electrical connection for the drain (not shown) of FET 20. A conductive, screen-printed contact 30 (preferably formed of graphite ink) connects a gate contact to a sensing layer 35 offset from the gate contact.

A layer 50 of an electrically insulating membrane anchor surrounds and dips down into aperture 20a to contact gate 35 while maintaining an aperture 20a. An electrically-insulating overcoat 60 covers the entire surface of substrate 10 except for aperture 20a. An ion-selective membrane 90 fills aperture 20a and is surrounded by a membrane well 100.

A membrane anchor 50 according to the present invention may be composed of homopolymers or copolymers of polymethyl methacrylate, polyvinyl chloride, polyvinyl acetate, cellulosics, polyurethanes, polyesters, vinyls, styrenes or polycarbonates. Commercially available materials of this format are: product number P7138, available from EMCA, Mamaroneck, N.Y.; product number 432SS, available from Acheson, Port Huron, Mich.; and product number M7400, available from Minico, Congers, N.Y.

The device of FIG. 1 may be constructed as follows. First, the substrate is annealed to remove all stress by placing it in an oven at highest expected process temperature for 2 hours and then turn oven off allowing the substrate to cool to room temperature slowly. The substrate is cleaned by sonication in the presence of isopropyl alcohol and vapor degreasing with trichlorotrifluorethane. FET 20 is mounted by dispensing adhesive into substrate recess 15, and then using a vacuum tool to pick up the chip and locate it in the recess. Then the adhesive is cured according to the manufacturer's recommendations. Standard precautions are taken to avoid static shock.

An underring is screen-printed around the chip as an insulative bridge, using a screen with a mesh, angle, and emulsion as is known in the industry. An insulating ink suitable for screen printing is used and the insulating ink cured according to manufacturers recommendations. Graphite is screen-printed as the sensing media over the metallized sensing pads of the gate contact on FET 20, curing the ink according to manufacturers recommendations. Insulating material 60 is next screen printed onto chip 20 and overlapping substrate 10, leaving sensor areas and contact pads uncovered. This insulating layer protects sensitive electronics of the semiconductor from adverse environments. Silver conductive runs connecting to the source and drain of FET 20 are screen-printed. Insulative overcoat material 60 is screen-printed and cured after screen printing and curing layer 50 of the membrane anchor to protect circuitry while also defining the sensing areas.

The substrate is then prepared for membrane application by rinsing sensing areas with a solvent such as trichlorotrifluoroethane, methyl ethyl ketone (MEK), or tetrahydrofuran (THF) to remove particulate matter from surface and allowing all remaining solvent to evaporate. The surface of the substrate is visualized with a microscope at approximately 50× magnification. An appropriate membrane formulation is applied to well 100 using a microliter syringe, onto sensing area within well 20a. The drop size is approximately 0.1 microliter. One to several drops may be applied, to obtain desired thickness of membrane 90. If multiple drops are used, each application is allowed to partially dry before the next one is applied. The membrane is cured for a period appropriate to membrane 90.

In order to test the sensing element, membrane 90 is conditioned by soaking in the appropriate ionic solution, for a period of time. The sensor is immersed in alternating solutions containing varying amounts of the appropriate analyte and an ionic strength adjuster to maintain constant solution ionic strength. The solutions are maintained at 25 degrees centigrade with a water bath and jacketed beakers. Using a pH meter in the "millivolt" mode, the potentials generated by the sensing elements are monitored. A saturated calomel electrode is employed as the reference element. Response time, drift, slope and correlation are observed.

Although this embodiment retains some metallization at the surface of substrate 20 in proximity of the analyte, the membrane anchor formed by layer 50 and the minimization of metalization on surface 10a permits a longer useful life than is exhibited by devices lacking these features.

Figure 2:
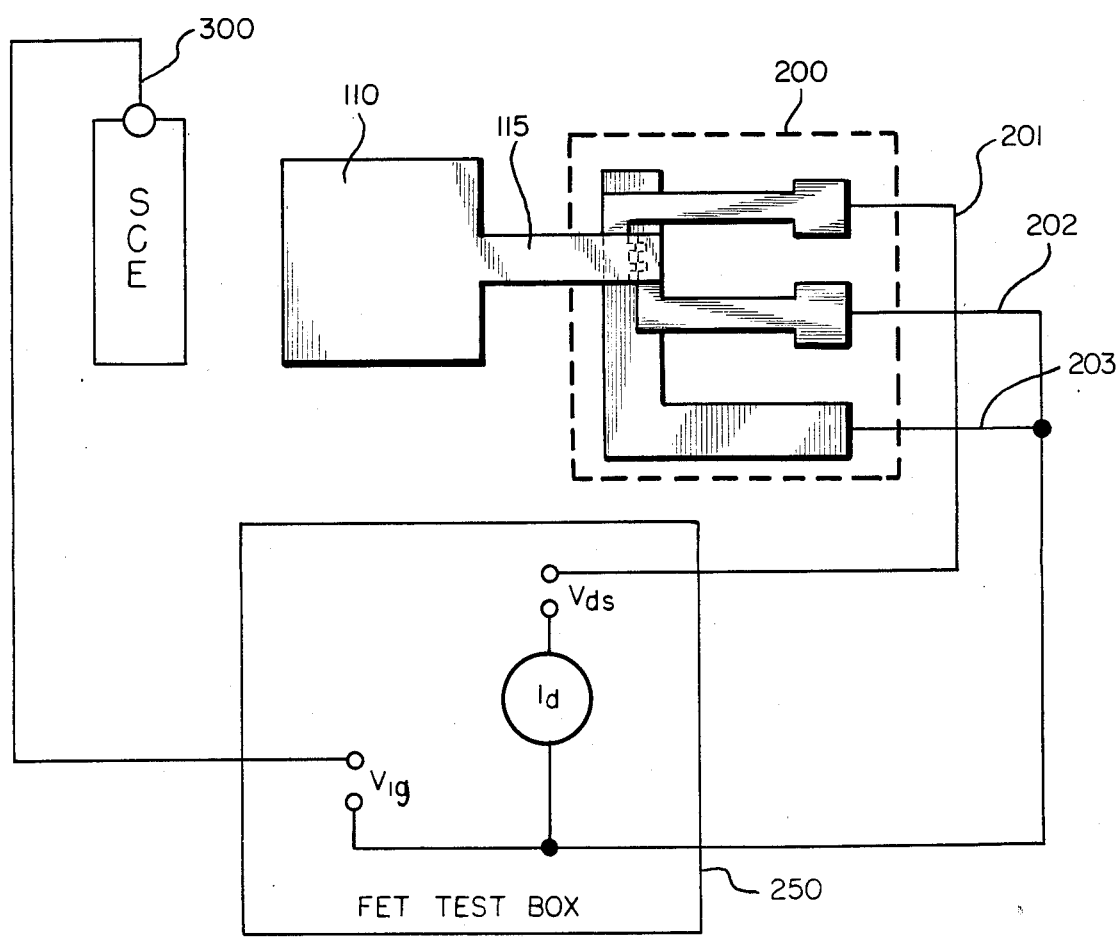
FIG. 2 is a schematic view of a preferred embodiment of a FET device according to the present invention.

In FIG. 2, a preferred embodiment of a FET device according to the present invention is schematically depicted. In this device a graphite pad 110 connects a sensing area to gate 115 of FET 200. FET 200 may thus be placed away from the well in which the analyte is placed or even on the reverse surface of the substrate by connecting a FET test box to source lead 201, drain lead 202 and bulk lead 203 of FET 200 and to a standard calomel electrode 300, the device may be used as an ion-selective electrode.

The $V_{ds}$ of a FET test box 250 is set at a constant value of approximately 2 volts. The $I_d$ is fixed at a value of $-50$ microamps. The frit of electrode 300 and the membrane area over the graphite are completely immersed into a test solution. The gate voltage is read in millivolts. As the concentration of an ion changes, the potential of the membrane changes according to the Nernst equation. The FET box is configured to adjust the $V_g$ (gate voltage) proportionally to the membrane potential change, such that a constant $I_d$ is maintained. The $V_g$ adjustment is used in the Nernst equation as the negative equivalent of membrane potential.

The membranes useful in sensing element and FET embodiments of the present invention may be prepared as follows:

For the sensing element embodiments (i.e. those not having an active device mounted on the first surface) a pH membrane may be prepared by dissolving: 20 mg tridodecylamine (ionophore), 132 mg dibutyl sebacate (plasticizer), 51 mg polyvinyl (PVC) and 1.4 mg sodium tetraphenylboron in 1 ml tetrahydrofuran (THF).

A potassium membrane may be prepared by dissolving 2.0 mg valinomylin (ionophore), 140 mg di-2-ethylhexyl adipate (plasticizer) and 60 mg PVC in 1 ml THF.

A sodium membrane may be prepared by preparing a stock PVC/THF solution of 33.0 mg PVC in 1 ml THF and dissolving 41.8 mg o-nitrophenyl octylether (plasticizer), 1.0 mg sodium tetraphenylboron, and 4.7 mg monensin methylester (ionophore) in 0.2 ml of the stock PVC/THF solution.

For both sensing element embodiments and for FET embodiments (i.e. those having an active device mounted on the first surface), a calcium membrane may be prepared using a stock PVC/THF solution of 13.2 mg PVC in 0.4 ml THF and dissolving 41.8 mg o-nitrophenyl octylether, 0.47 mg sodium tetraphenylboron and 4.7 mg Fluka #21192 calcium ionophore in 0.2 ml of the stock PVC/THF solution.

For FET embodiments, a potassium membrane may be prepared by dissolving 41.8 mg o-nitrophenyl octylether, 0.47 mg sodium tetraphenylboron and 4.7 mg valinomycin in 0.2 ml of the same stock PVC/THF solution described for the calcium membrane.

Materials useful in the construction of ion-selective electrodes as described herein may be obtained from the following sources. PVC from Polysciences Incorporated, Warrington, Pa.; THF from Aldrich Chemical Company, Milwaukee, Wis.; sodium tetraphenylboron from Aldrich Chemical Company, Milwaukee, Wis.; dibutyl sebacate from Kodak Chemicals, Rochester, N.Y.; tridodecylamine from Kodak Chemicals, Rochester, N.Y.; valinomycin from Sigma Chemical Company, St. Louis, Mo.; di-2-ethylhexyladipate from Polysciences, Inc., Warrington, Pa.; o-nitrophenyloctylether from Fluka Chemical Corporation, Ronkonkona, N.Y.; monensin methyl ester from Calbiochem Biochemicals, San Diego, Calif. and Calcium Ionophore #21192, Fluka Chemical Corp., Ronkonkona, N.Y.

A useful substrate material for embodiments of the present invention is a thermoplastic polyester resin for injection molding available from General Electric Corporation, Albany, N.Y., as the product Valox TM 865. Screens for screen printing according to the present inventor may be obtained from Microcircuit Engineering Corporation Mount Holly, N.J. as 200MESH W/1.655 wire @30 degree angle using type ES emulsion. A graphite ink useful according to the present invention is available from Acheson Colloids Company, Port Huron, Mich. as product #423SS.

In one embodiment of the present invention the ion-selective electrode, as illustrated in FIG. 3, a plastic substrate 700 holds five electrical pins (701, 702, 703, 704 and 705), a reference electrode 710, five ion-selective-electrode membranes (751, 752, 753, 754 and 755), a first insulating layer 730 have apertures defining respective spaces 740 for reference electrode 710 and 741–745 respectively for sensing electrodes 721–725, cylindrical apertures 731–736 pass through substrate 700, and conductors (721–726) between the pins (701–706) and the reference electrode and the membranes. Reference electrode 710 is a small silver/silver chloride square. It is inserted in the bottom of substrate 700 with a potassium chloride gel above it. The gel is exposed to the test solutions via a small 0.005 inch diameter hole in the top surface of substrate 700.

Deposited above layer 730, overlapping the respective perimeters of spaces 741–745 are square membrane anchors 761, 762, 763, 764 and 765, each of which has a central, square aperture respectively beneath membranes 751–755. A second insulating layer 760 is approximately identical to layer 730 in configuration, including the location and size of apertures 741–745, but lies above membrane anchors 761–765.

The top side of substrate 700 is covered with conductive carbon traces from the pins to the area where the ion-selective-electrode membranes are placed. An insulating pattern is formed over the conductive traces to protect them. The ion-selective electrode membranes 721–723 are placed above the insulating and conductive traces.

Moreover, although a single membrane anchor layer has been described herein, it is contemplated that a plurality of membrane anchor layers may be intersolubilized with the ion-sensitive membrane and interleaved with insulating layers to provide as circuitous a path for moisture to reach any metallization as may be practical or desired.

Furthermore, in addition to those materials listed herein, thermoset materials suitable for tight adherence to a substrate and for insulating layers include, for example, epoxies, urethanes, phenolics, and silicones. In addition to the thermoplastic material employed herein, the following thermoplastic materials, for example, may be useful for intersolubilization with ion-sensitive membranes, e.g., PVC, PVAc, PVAl, cellulosics, acrylics, urethanes, PVDF, and polyesters. In general, anchor materials which are soluble in the same solvent or the membrane may be intersolubilized with the membrane. Exceptions to this general rule involve materials which may not be intersolubilized because of mismatch in crystallinity, packing, or interaction parameters as defined by, for example: Flory, "Principles of Polymer Chemistry," Cornell University Press, Ithaca, New York, (1953); Huggins, Polym. J., 4, 511 (1973); Hildebrand, Ind. Eng. Chem. Fund., 17, 365 (1978); and Hansen, J. Paint Technol., 39, 511 (1967).

Therefore, it is intended that the present invention include all such variations and improvements which come within the scope of the invention as claimed.

We claim:

1. An ion-selective electrode comprising:
   an electrically insulating substrate having a substantially planar surface and;
   a conductor on said surface;
   an ion-selective membrane affixed to said conductor, for sensing a potential, and
   an electrically insulating layer comprising a first insulating stratum affixed to said first surface and surrounding said ion selective membrane, and a second insulating stratum surrounding and intersolubilized with said ion-selective membrane.

2. The ion-selective electrode as recited in claim 1 wherein said means for sensing comprises a field effect transistor and a conductive termination coupled to a gate of said field effect transistor.

3. An ion-selective membrane anchor for containment of ion-selective membranes in substantially planar ion selective electrodes having a conductive sensing area contacted by an ion-selective membrane and having a substantially planar surface surrounding said sensing area comprising:
   a first insulating stratum affixed to said planar surface surrounding said conductive sensing area of said ion-selective electrode;
   a second insulating stratum affixed to said first stratum and intersolubilized with said ion-selective membrane of said sensing area.

4. The ion-selective electrode of claim 1 wherein said second insulating stratum comprises a solvent sensitive material whereby solvent in said ion-selective membrane partially dissolves said material.

5. The ion-selective electrode of claim 4 wherein said second insulating stratum is a thermoplastic polymer.

6. The ion-selective electrode of claim 1 wherein said electrically insulating layer further comprises a third insulating stratum covering said first and second stratums.

7. The ion-selective membrane anchor of claim 3 wherein said second insulating stratum comprises a solvent sensitive material whereby solvent in said ion-selective membrane partially dissolves said material.

8. The ion-selective membrane anchor of claim 7 wherein said second insulating stratum is a thermoplastic polymer.

9. The ion-selective membrane anchor of claim 3 which further comprises a third insulating stratum covering said first and second insulating stratums.

* * * * *